United States Patent [19]

Nielsen

[11] 4,276,732
[45] Jul. 7, 1981

[54] DEVICE FOR KILLING MOSS

[75] Inventor: James W. Nielsen, Newport, Oreg.

[73] Assignee: Sharon G. Nielsen, Newport, Oreg.

[21] Appl. No.: 69,291

[22] Filed: Aug. 24, 1979

[51] Int. Cl.³ ............................................. B27K 3/22
[52] U.S. Cl. ....................................... 52/517; 52/11;
422/291; 424/16
[58] Field of Search ..................................... 52/11–15,
52/101, 517; 422/291; 424/16; 106/18.35; 71/3,
65

[56] References Cited

U.S. PATENT DOCUMENTS

| 3,479,130 | 11/1969 | Rapaport | 52/101 X |
| 3,494,727 | 2/1970 | Rapaport | 52/517 |
| 3,507,396 | 4/1970 | Homa | 52/12 X |
| 3,513,586 | 5/1970 | Meyer | 52/101 X |

Primary Examiner—J. Karl Bell
Attorney, Agent, or Firm—Klarquist, Sparkman, Campbell, Leigh, Whinston & Dellett

[57] ABSTRACT

A device for killing moss on rooftops comprises an elongated bimetallic trough for horizontal positioning along a rooftop to catch rainwater. In one embodiment the walls of the trough include a layer of copper and a layer of lead sandwiched together. Small holes through such layers, and spaced apart in rows along a wall of the trough, slowly drain the rainwater onto the rooftop. As the water passes through the holes, contacting the junction of the lead and copper layers, an electrolytic action occurs in which ions of the metal dissolve into the water. The resultant electrolyte kills the moss. Another embodiment comprises a plastic trough having holes in one side and containing pieces of lead and copper.

21 Claims, 11 Drawing Figures

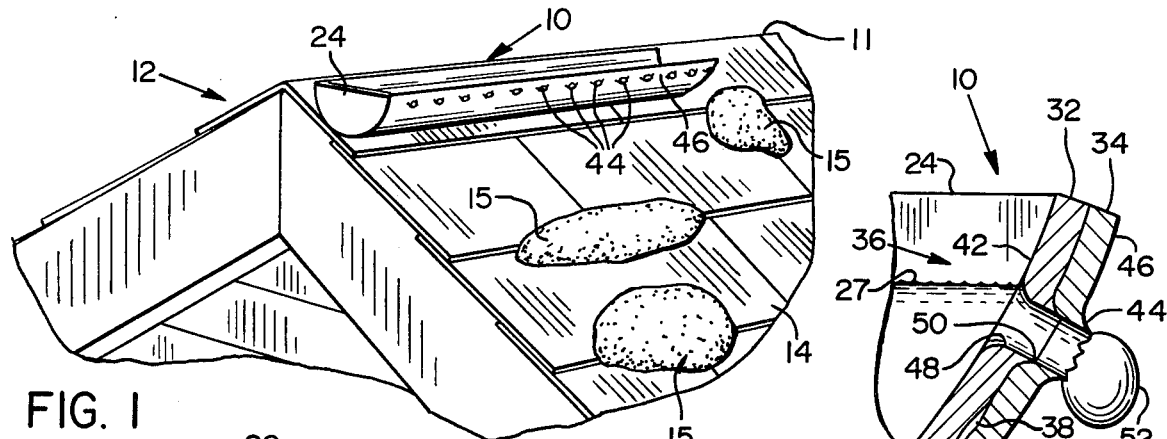

DEVICE FOR KILLING MOSS

BACKGROUND OF THE INVENTION

The invention relates generally to biocidal ionic solutions and more particularly to apparatus for producing metallic electrolytes for killing moss.

In very moist climates the growth of moss on rooftops, particularly their shaded portions, is a problem. Such moss is unsightly, does not allow the roof to dry properly, and can cause rotting of wood shingles and cracking of composition shingles. This permits water leakage which can damage the support structure of the roof, the ceiling insulation and other ceiling materials. Such damage is very expensive to repair. Consequently, it is desirable to kill moss growing on rooftops and prevent its return.

Manual removal of moss from rooftops is difficult, dangerous and provides only a temporary solution to the problem. The moss regrows within a few weeks from spores remaining beneath the shingles.

Attempts have been made to control moss growth chemically. Ions of certain metallic elements, such as lead, zinc or copper, are known to have biocidal characteristics. At least one such metal, copper, has been used to combat moss, but without great success. For example, nailing a flat strip of copper to a roof has been tried, but has proven unsatisfactory because it can take many months before any reduction in moss occurs. Powdered copper compounds, such as copper sulfate powder sprinkled on the roof, act more quickly than the copper strip, but usually wash off within one month and thus, require frequent reapplications. S. L. Rapaport has previously proposed, in U.S. Pat. No. 3,479,130, mounting flat bimetallic strips horizontally along a rooftop to inhibit microbial or fungal growths which darken rooftops in semitropical and tropical climates. Rapaport discloses the use of two metals, such as copper and lead, between which an electrolytic action results when rainwater contacts the metals. Such action dissolves ions of the metals into the water to create a solution which kills the microbes and fungus. To obtain adequate coverage of a rooftop multiple strips are used, such strips being vertically spaced four to ten shingles apart.

However, installing multiple strips is time consuming and results in a aesthetically unappealing horizontally striped appearance of the roof. Rapaport's subsequent proposal, in U.S. Pat. No. 3,494,727, to imbed chips of ion-producing metal into the surface of roofing material meets the latter objection, but would require re-roofing existing buildings at substantial expense, not to mention the increased cost of producing such roofing material.

It would be preferable to have a means for killing moss on rooftops which is inexpensive, easy to apply, fast-acting, long-lasting and not aesthetically unappealing.

SUMMARY OF THE INVENTION

It is a principal object of the invention to produce a stronger biocidal ionic solution which will act more quickly to kill moss and will be effective even when dispersed over large areas.

Another object of the invention as aforementioned is to inhibit growth of moss for many years after a single application. A further object is to provide a moss-killing device that is inexpensive to construct and install.

Yet another object is to provide an aesthetically inconspicuous device for killing moss.

According to the invention, a device for killing moss on rooftops comprises a trough containing biocidal ion-producing metal for catching rainwater, dissolving metal ions into the water and slowly draining such water onto the surface of the roof.

The ion-producing characteristics of the device are enhanced in several ways. By using two metals, such as lead and copper, which react galvanically at their junction in the presence of water, biocidal ions are dissolved more quickly into the water. By using a trough to collect rainwater and to hold the water in contact with the two metals, the duration of the galvanic reaction is prolonged so that more ions are dissolved into the water than are dissolved during the relatively brief contact of rainwater with metal strips.

In one embodiment, the trough can have multi-layered metal side and bottom walls defining a generally U-shaped cross-section. Small holes or perforations extending through the sides or bottom of the trough permit water in the trough to contact the bimetallic junctions of the layers and provide means for gradually draining the resultant ionic solution onto the rooftop. Decreasing the size of the holes and increasing their number increases the strength of the solution, as does increasing the number of bimetallic surfaces exposed to the water.

Such a moss-killing device can be small, for example about one inch across the trough opening, and still be effective over a large area. Thus, a single such device, mounted inconspicuously along the roofline, can keep an entire roof panel free of moss. It has also been found that the biocidal solutions produced by such device will kill mildew.

The foregoing and other objects, features and advantages of the invention will become more apparent from the following detailed description of several preferred embodiments which proceeds with reference to the drawing.

BRIEF DESCRIPTION OF THE DRAWING

FIG. 1 is a perspective view of a portion of a conventional rooftop having a moss-killing trough according to the invention mounted thereon.

FIG. 2 is a cross-sectional view of a two-layered embodiment of a trough according to the invention, mounted on a rooftop.

FIG. 3 is a top plan view to the trough of FIG. 2, shown prior to folding of its walls into the form of a trough.

FIG. 4 is an enlarged partial cross-sectional view of the trough of FIG. 2 showing details of the holes.

FIGS. 5 and 6 are cross-sectional views of three-layered embodiments of a trough according to the invention.

FIG. 7 is a cross-sectional view of a split-pipe trough according to the invention with bimetallic chips placed therein.

FIG. 8 shows a cross-sectional view of a two-layered trough according to the invention in which one wall is flattened for insertion beneath a roof shingle.

FIG. 9 shows a variation of the trough of FIG. 8 in which the two layers are separated to define two troughs.

FIGS. 10 and 11 are top plan views of the trough of FIG. 9 showing examples of alternative drainage means.

DETAILED DESCRIPTION OF THE PREFERRED EMBODIMENTS

General Characteristics

Referring to FIG. 1, a device for killing moss comprises a trough 10 which is preferably mounted horizontally along the ridge 11 of roof 12 for pooling rainwater to treat a roof panel 14 covered by patches of moss 15. The trough ordinarily extends along the entire length of the roof panel, but can be made in any length desired.

Referring to FIG. 2, the trough has side walls 16 and 18 connected by a bottom wall 20 to define a generally U-shaped cross-section having an upwardly facing opening 22 for catching and pooling rainwater. Each end of the trough is closed by an end wall 24 (FIG. 1). Drainage means for gradually draining the rainwater onto the roof can be as simple as allowing the trough to overflow when it is full. Other forms of drainage means are described hereinafter.

The trough can be attached to the roof by nails 26 pounded through side wall 16 near the ridge of the roof at suitable intervals along its length. Since the trough can be relatively small, for example less than one inch (2.5 cm.) across opening 22, nails 26 are usually sufficient to support the trough even when filled with water 27. When a larger trough size is required for a large roof panel, braces 28 (FIG. 7) can be added on the lower side of the trough.

The device also includes quantities of at least two elemental metals. Such metals should be capable of reacting galvanically in the presence of water to produce water soluble ions. The ion of at least one such metal must have biocidal characteristics that are effective on moss. Lead and copper together provide these characteristics, although other combinations of metals, such as zinc and iron, may work as well. One or more such metals can be incorporated into the body of the trough or can be dispersed on the trough, which can be made, for example, of plastic. Several configurations of such troughs are described in the following alternative embodiments.

FIG. 2 Embodiment

In the trough of FIG. 2, the walls of the trough are made of ion-producing metals. Such a trough can be constructed of an elongated, multi-layered, bimetallic strip 30 (FIG. 3) which has been partially folded or cupped along its length to achieve the U-shaped cross-section of FIG. 2. The strip is formed of at least two layers 32, 34 of different metals, such as copper and lead. Small holes 36 are punched through the strip before folding it to expose the junctions of the layers to the captured rainwater and to slowly drain the water onto the rooftop.

Lead sheets of 16-gauge thickness and copper sheets of 14-gauge thickness provide layers of suitable thickness, although these dimensions can be varied.

Referring to FIG. 4, the layers need not be bonded together because nails 26 and punched holes 36 provide sufficient contact between the layers for electrolysis to occur around the holes. In addition, any gaps 38 between the layers will admit water and air into regions of contact between the holes where electrolysis can also occur.

Holes 36 are preferably positioned in a row extending along side wall 18. Multiple rows of holes can also be used, as shown in FIG. 6. The holes are punched with a one-penny nail or a similarly sized punch. This operation produces holes having a diameter of about 1/32" (0.8 mm). Punching the holes from the inner surface 42 of the trough squeezes the layers of metal together around each hole to form regions of contact between adjacent faces of the layers. It also produces a droplet-forming nipple 44 on the outer surface 46 of the trough.

Thus, a cylindrical surface 48 defines an exposed bimetallic junction 50 at which electrolytic action can occur when water 27 is present. The small diameter of the holes, aided by surface tension of the water as it forms droplets 52 in the nipples, controls the rate of leakage of water from the trough so that water remains in prolonged contact with the bimetallic junction and can thus dissolve more of the metal than otherwise. Such construction results in stronger biocidal solutions than were available from previous metal strip designs.

FIG. 5 Embodiment

In trough 10a of FIG. 5 an inner layer 52 of copper is sandwiched between two outer layers 54, 56 of lead to form triple-layered trough walls. The lead layers can be separate sheets or, as shown in trough 10b of FIG. 6, can be a single sheet folded around one edge of the copper sheet. In all other respects the troughs of FIGS. 5 and 6 resemble that of FIG. 2. The three-layer construction is somewhat preferred over the two layer design in that it provides two lead-copper junctions 60, 62 at which galvanic action can occur in the presence of water, but it is more costly to construct.

FIG. 7 Embodiment

In FIG. 7 the trough 10c itself can be either metallic or nonmetallic. For example, the trough can be made of split plastic pipe, and the ion-producing metals are chips or pieces 64 of lead and copper deposited in the trough, preferably with the bimetallic pieces in contact with one another. Alternatively, the trough can be made of split pipe of one metal, such as copper, having pieces of a second metal, such as lead, dispersed therein.

This design is particularly useful on large roof-tops which require a larger trough to capture and release a greater quantity of moss-killing solution than is required by small rooftops. Using split pipe rather than a multi-layered metal trough reduces the cost of materials for large troughs. It also permits replenishment of the ion-producing metals without replacing the entire trough.

Ordinarily, braces 28 are used to mount trough 10c. However, small split-pipe troughs can be mounted using nails.

Holes 36c are preferably drilled in plastic pipe troughs because the elasticity of the plastic makes punching such holes difficult. Alternatively, vertical slots can be cut in wall 18c as shown in FIG. 10 to provide a controlled drainage means.

FIG. 8 Embodiment

Trough 10d in FIG. 8 is similar to trough 10 of FIG. 2 except that wall 16d of FIG. 8 is straight rather than curved so that it can fit beneath the lower edge of ridge shingle 66.

FIG. 9 Embodiment

Trough 10e in FIG. 9 is similar to trough 10d of FIG. 8 except that layers 32e and 34e in FIG. 8 only contact each other in the region 68 of wall 16e. Layer 32e is curved upwardly about an axis of curvature which is closer to ridge 11 than the axis of upward curvature of layer 34e. Thus, trough 10e provides two upwardly-open trough portions 70, 72 rather than the single trough of the FIG. 2 embodiment.

Rainwater is collected in a lower pool 27a by trough portion 70 and in an upper pool 27b by trough portion 72. The water in pool 27a contacts both layers 32e and 34e in region 68 to facilitate electrolysis of the two metals. Such water gradually leaks through holes 36e onto the rooftop, carrying ions of the two metals with it. Water in pool 27b gradually drains through holes 36f into pool 27e. By making holes 36f smaller than holes 36e, pool 27b drains more slowly than pool 27a. Thus, the upper pool replenishes the lower pool and extends the time over which water in the lower pool dissolves the metal and drains onto the rooftop.

In FIG. 10 vertical notches 74 replace holes 36e, 36f of the trough of FIG. 9. In FIG. 11, a scalloped upper edge 76 of layer 32e replaces holes 36f of FIG. 6. Each undulation in layer 32e forms a lip 78 which allows water to pour into the pool below.

Numerous other drainage means for controllably releasing water onto the roof can also be used. Examples not shown in the drawings include long narrow slots in a side or bottom wall of the trough, overflow lips similar to lips 78, and a pervious side or bottom wall.

FIGS. 10 and 11 also depict a unitary end wall 80 which can substitute for end wall 24. Such a wall is formed by cutting layers 32, 34 along dashed lines 82, 84 in FIG. 3, removing portion 86, and folding portions 88, 90 upwardly until they meet at corner 92. Some leakage at corner 92 is permissible.

Having illustrated and described several preferred embodiments of the invention, it should be apparent to those skilled in the art that the invention may be modified in arrangement and detail. I claim as my invention all such modifications as come within the true spirit and scope of the following claims.

I claim:

1. A device for killing moss on roofs, comprising a trough for positioning along a rooftop to receive and pool water; said trough including at least two elemental metals operable to form a biocidal electrolyte in the presence of water.

2. A device according to claim 1 including drainage means for providing a controlled release of said water from said trough such that the resultant biocidal electrolyte is spread over the roof to destroy existing moss and inhibit the growth of additional moss.

3. A device according to claim 2 in which said drainage means includes overflow lips along an upper edge of a side wall of said trough.

4. A device according to claim 2 in which said drainage means includes openings extending through a wall of said trough.

5. A device according to claim 4 in which said openings include notches along an upper edge of a side wall of said trough.

6. A device according to claim 4 in which said openings include perforations through said wall.

7. A device according to claim 6 in which said perforations include holes which define droplet forming means.

8. A device according to claim 4 in which said trough includes a wall comprising at least one layer of a first of said metals and at least one layer of a second of said metals;
inwardly-opposed faces of said layers defining regions of contact between said first and second metals.

9. A device according to claim 8 in which said wall includes three layers, an inner layer of a first metal being sandwiched between outer layers of a second metal.

10. A device according to claim 8 or 9 in which said drainage means includes small holes punched through said wall from the inner surface to the outer surface thereof.

11. A device according to claim 1 or 4 in which at least one of said metals defines a wall of said trough.

12. A device according to claim 1 wherein said metals have regions of contact therebetween, said regions being exposed to said water.

13. A device according to claim 1 in which said trough includes a wall comprising at least one layer of a first of said metals and at least one layer of a second of said metals;
inwardly-opposed faces of said layers defining regions of contact between said first and second metals.

14. A device according to claim 1 wherein said trough includes a side wall portion adapted for insertion beneath the lower edge of a shingle on a rooftop.

15. A device according to claim 1 in which said trough includes:
wall means defining upper and lower trough portions;
first drainage means for providing a controlled release of water from the upper trough portion into the lower trough portion; and
second drainage means for providing a controlled release of the resultant biocidal electrolyte onto the roof.

16. A device according to claim 15 in which said wall means includes a first wall defining said upper trough portion composed of a first of said metals and a second wall defining said lower trough portion composed of a second of said metals, said first and second walls being in metal-to-metal contact in a region exposed to water collected in said lower trough portion.

17. A device according to claim 1 including intermingled pieces of said metals dispersed within the trough.

18. A device according to claim 1 in which one of said metals is copper and another of said metals is lead.

19. A device according to claim 1 in which one of said metals is copper.

20. A device according to claim 1 in which one of said metals is lead.

21. A device according to claim 1 including a wall composed of a first of said metals and having pieces of a second of said metals dispersed within the trough in contact with said wall.

* * * * *